(12) United States Patent
Bouvier et al.

(10) Patent No.: US 8,979,365 B2
(45) Date of Patent: Mar. 17, 2015

(54) DEVICE FOR SUPPORTING ELEMENTS FOR CONNECTING A MOBILE X-RAY MACHINE AND X-RAY MACHINE PROVIDED WITH SUCH A SUPPORTING DEVICE

(75) Inventors: Bernard Bouvier, Eragny sur Oise (FR); Bruno Galloni, Saint Lubin des Joncherets (FR)

(73) Assignee: General Electric Company, Schenectady, NY (US)

( * ) Notice: Subject to any disclaimer, the term of this patent is extended or adjusted under 35 U.S.C. 154(b) by 211 days.

(21) Appl. No.: 13/423,547

(22) Filed: Mar. 19, 2012

(65) Prior Publication Data

US 2012/0321050 A1 Dec. 20, 2012

(30) Foreign Application Priority Data

Mar. 24, 2011 (FR) ..................................... 11 52437

(51) Int. Cl.
*A61B 6/00* (2006.01)

(52) U.S. Cl.
CPC .............. *A61B 6/4464* (2013.01); *A61B 6/4405* (2013.01); *A61B 6/56* (2013.01); *A61B 6/4441* (2013.01); *A61B 6/504* (2013.01); *A61B 6/4423* (2013.01)
USPC ........................................................ 378/194

(58) Field of Classification Search
CPC ...... A61B 6/4405; A61B 6/4464; A61B 6/56; A61B 6/4423; A61B 6/4441
USPC ............................................ 378/194; 59/78.1
See application file for complete search history.

(56) References Cited

U.S. PATENT DOCUMENTS

| | | | | | |
|---|---|---|---|---|---|
| 3,118,066 | A | * | 1/1964 | Thomas et al. | 378/194 |
| 3,551,612 | A | * | 12/1970 | Guentner | 378/194 |
| 4,658,577 | A | * | 4/1987 | Klein | 59/78.1 |
| 5,436,461 | A | * | 7/1995 | Saffer et al. | 250/522.1 |
| 7,604,403 | B2 | | 10/2009 | Yi | |
| 2006/0083353 | A1 | * | 4/2006 | Boomgaarden | 378/196 |
| 2009/0147924 | A1 | * | 6/2009 | Gross et al. | 378/194 |
| 2009/0154652 | A1 | * | 6/2009 | Yi | 378/194 |
| 2009/0180595 | A1 | * | 7/2009 | Spahn | 378/197 |
| 2010/0296632 | A1 | | 11/2010 | Bouvier | |
| 2010/0299014 | A1 | | 11/2010 | Bouvier | |
| 2012/0085078 | A1 | * | 4/2012 | Rijken et al. | 59/78.1 |

FOREIGN PATENT DOCUMENTS

| | | |
|---|---|---|
| CN | 1264476 C | 7/2006 |
| CN | 101455570 A | 6/2009 |
| FR | 2945724 A1 | 11/2010 |
| WO | 2006/095301 A1 | 9/2006 |

(Continued)

OTHER PUBLICATIONS

Search Report from corresponding FR Application No. 1152437, date as Sep. 9, 2011.
Unofficial translation of (SIPO)Chinese Office Action from CN Application No. 2012100976560, dated Jan. 21, 2014.
European Search Report and Written Opinion from EP Application No. 12160772.5 dated May 23, 2012.

(Continued)

*Primary Examiner* — Glen Kao
(74) *Attorney, Agent, or Firm* — GE Global Patent Operation; Marc A. Vivenzio

(57) ABSTRACT

A device for supporting elements connecting a mobile X-ray machine is provided. The device comprises a chain that can be deformed in a single plane configured to contain connection elements of a mobile X-ray machine.

18 Claims, 4 Drawing Sheets

(56) References Cited

FOREIGN PATENT DOCUMENTS

| WO | 2007/132419 | A2 | 11/2007 |
| WO | 2010/150172 | A2 | 12/2010 |

OTHER PUBLICATIONS

European Official Action from EP Application No. 12160772.5 dated Apr. 30, 2013.

* cited by examiner

DEVICE FOR SUPPORTING ELEMENTS FOR CONNECTING A MOBILE X-RAY MACHINE AND X-RAY MACHINE PROVIDED WITH SUCH A SUPPORTING DEVICE

BACKGROUND OF THE INVENTION

1. Field of the Invention

The field of invention relates generally to X-ray machines used in medical imaging. More particularly, the field of invention relates to the support of electrical cables that electrically connect such machines.

2. Description of Related Art

X-ray machines conventionally comprise an X-ray tube and an X-ray detector placed opposite of the X-ray tube in the direction of emission of the X-rays. The tube and the detector are usually placed on opposite ends of an arm.

Such machines are used for angiographic examinations with a diagnostic or interventional aim. During these examinations, it is necessary to take X-ray radiographs of an area of interest in the body of a patient. For this purpose, after the patient has been laid out on an examination table, the X-ray tube and the detector are brought to face the area to be radiographed.

There are several types of X-ray machines for producing radiographs. First, X-ray machines that are fixed to the ground and in which the arm supporting the X-ray tube and the detector comprise several degrees of freedom making it possible to position the X-ray beam facing the area of interest are known. This type of machine has a major drawback when radiography is only necessary at the beginning and end of the intervention. In the middle, access to the patient should take precedence. However, the machine, cannot be removed from the examination table when it is not being used. In particular, transferring the patient onto the examination table is hampered by the presence of this bulky system.

There are also X-ray machines called "surgical mobile units" that can be moved manually. In this case, they are mounted on a carriage that contains a certain number of batteries used to supply the X-ray tube with power. This type of apparatus is not suitable for angiographic examinations because the power available to the X-ray tube is no longer sufficient to obtain adequate image quality and, in particular, contrast. Moreover, this type of mobile X-ray machine does not allow complex angulations because the diameter of the arm supporting the tube and the detector is not big enough. Similarly, these mobile X-ray machines do not achieve sufficient rotation speeds to allow high quality, three-dimensional image reconstructions. Finally, even though the weight of such an apparatus is half as much as that of an X-ray machine designed for angiography, it remains very difficult to move because of its relatively large dimensions and weight, which can be up to about 300 kg (about 660 lbs).

In addition, X-ray machines for angiography are known that are suspended from the ceiling and can be moved on guide rails, via a movable carriage, for example with the aid of an electric motor. This type of machine also has several drawbacks. First, many systems are already attached to the ceiling around the examination table, thus the space around the patient is already cluttered, which makes it difficult to install guide rails. Secondly, mounting an X-ray machine on the ceiling considerably increases the risk of opportunistic contamination of the patient. Specifically, because of the difficulty of cleaning the rails, particles are likely to fall and contaminate the patient when the apparatus is sliding on the rails. Moreover, in certain operating rooms, a sterile laminar flow is generated above the patient. In this case, the flow is likely to blow the particles present on the rail which can then enter the laminar flow and reach the patient.

To alleviate these various drawbacks, it has been proposed to mount the X-ray machine on a mobile device mounted on wheels driven by drive motors controlled automatically under the control of a navigation system. It has been found that such a system is particularly effective for positioning the X-ray tube and the detector around the area of interest and to remove it when it is no longer in use, in order to free up the space around the examination table.

However, this X-ray machine is connected to cabinets, that are in an equipment room far from the examination room, by a certain number of connection elements, such as cables and pipes providing the electrical supply to the machine, providing its cooling and providing data interchanges with the machine. In the operating room, these elements travel high up and are placed in a retaining sheath. Since the machine is capable of being moved into various locations of the room, it is necessary to provide a sufficient length of connection elements to prevent its movement from being restricted. Therefore, in certain positions of the machine, the cable retained in its sheath forms loops which hang, clutter the operating room, and are likely to constitute obstacles.

In view of the foregoing, the object of the embodiments of the invention is to propose a supporting device that makes it possible to effectively guide the connection elements of an X-ray machine.

BRIEF SUMMARY OF THE INVENTION

According to one embodiment, a device for supporting elements connecting a mobile X-ray machine is provided. The device comprises a chain that can be deformed in a single plane configured to contain connection elements of a mobile X-ray machine.

According to another embodiment of the present invention, an X-ray machine is provided. The X-ray machine comprises an X-ray tube, an X-ray detector placed opposite the X-ray tube in the direction of emission of the X-rays, a movable device onto which the X-ray tube and the X-ray detector are mounted, and an arm erected from the movable device. The X-ray machine further comprises a device for supporting elements connecting the X-ray machine, the device comprising a chain that can be deformed in a single horizontal plane, the chain configured to contain connection elements of the X-ray machine and configured to attach at one end to the arm.

Further aspects, advantages and features of the present invention are apparent from the dependent claims, the description and the accompanying drawings.

BRIEF DESCRIPTION OF THE SEVERAL VIEWS OF THE DRAWINGS

Embodiments of the present invention will now be described, by way of example only, with reference to the accompanying drawings, in which.

DETAILED DESCRIPTION OF THE INVENTION

Figure 1:
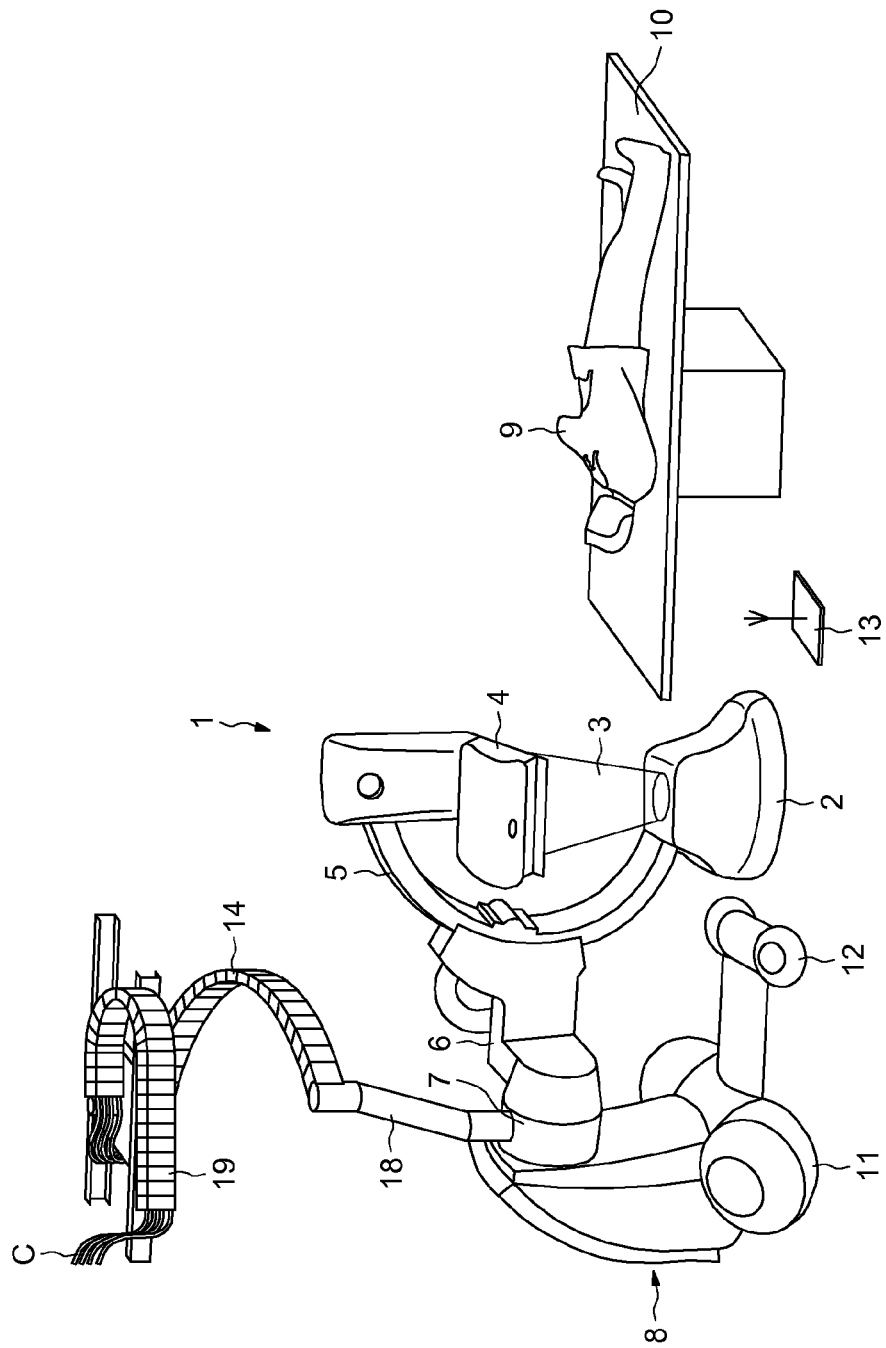
FIG. 1 is a schematic view of an X-ray machine furnished with a device for supporting connection elements according to an embodiment of the present invention.

FIG. 1 illustrates an X-ray machine 1 of the vascular type. As can be seen, this machine 1 essentially comprises an X-ray tube 2, capable of emitting a beam 3 of X-rays in an emission direction, and an X-ray detector 4. The tube 2 and the detector 4 are each placed at the two mutually opposed ends of an arm 5, which in this instance takes the form of an arch so that the X-rays emitted by the tube 2 are incident on the detector 4. The arm 5 is mounted so as to slide on a second arm 6 mounted rotatingly on a fixed support 7, which itself is mounted on a mobile device 8. Therefore, the support 7, the rotating arm 6 and the arm 5 are all articulated relative to one another so that the X-ray machine can move in three dimensions and thus produce images of an organ to be examined from various angles.

During a radiography, the tube 2 and the detector 4 are brought to face an area of interest in the body 9 of a patient laid out on an examination table 10 so that, when the area of interest is interposed between the X-ray tube 2 and the detector 4, it is irradiated by the X-rays and the detector 4 produces data representative of characteristics of the interposed area of interest.

The mobile device 8 comprises, in the embodiment shown, a rolling system comprising two lateral driving and steering wheels 11 placed at the rear, and two free front wheels 12, the driving wheels being associated with driving means comprising a steering motor coupled to a driving motor. The mobile device 8 is a programmable device and is associated with a navigation system capable, for example, of communicating via radioelectric link with identification devices 13 placed in the operating room in order to allow the machine 10 to locate itself precisely in the room and, notably, relative to the examination table 10.

Finally, FIG. 1 shows that the machine 1 is connected to remote cabinets, situated in an equipment room, by a set of connection elements C. These connection elements comprise a set of power and electrical connection cables dedicated to supplying the machine with electric power, of ducts in which a cooling fluid circulates, water in this instance, and of data transmission channels, of the optical fibre type.

As can be conceived, the length of the connection elements must be sufficient to allow the machine 10 to move in the room and, notably, to allow it to be moved into an out-of-the-way parking zone when the machine is not in use, and to allow it to be positioned around the patient during the intervention. The connection elements C are placed in a supporting device 14 comprising a chain of articulated links capable of confining the bundle of connection elements in a horizontal plane situated in the vicinity of the ceiling of an operating or examination room.

Figure 2:
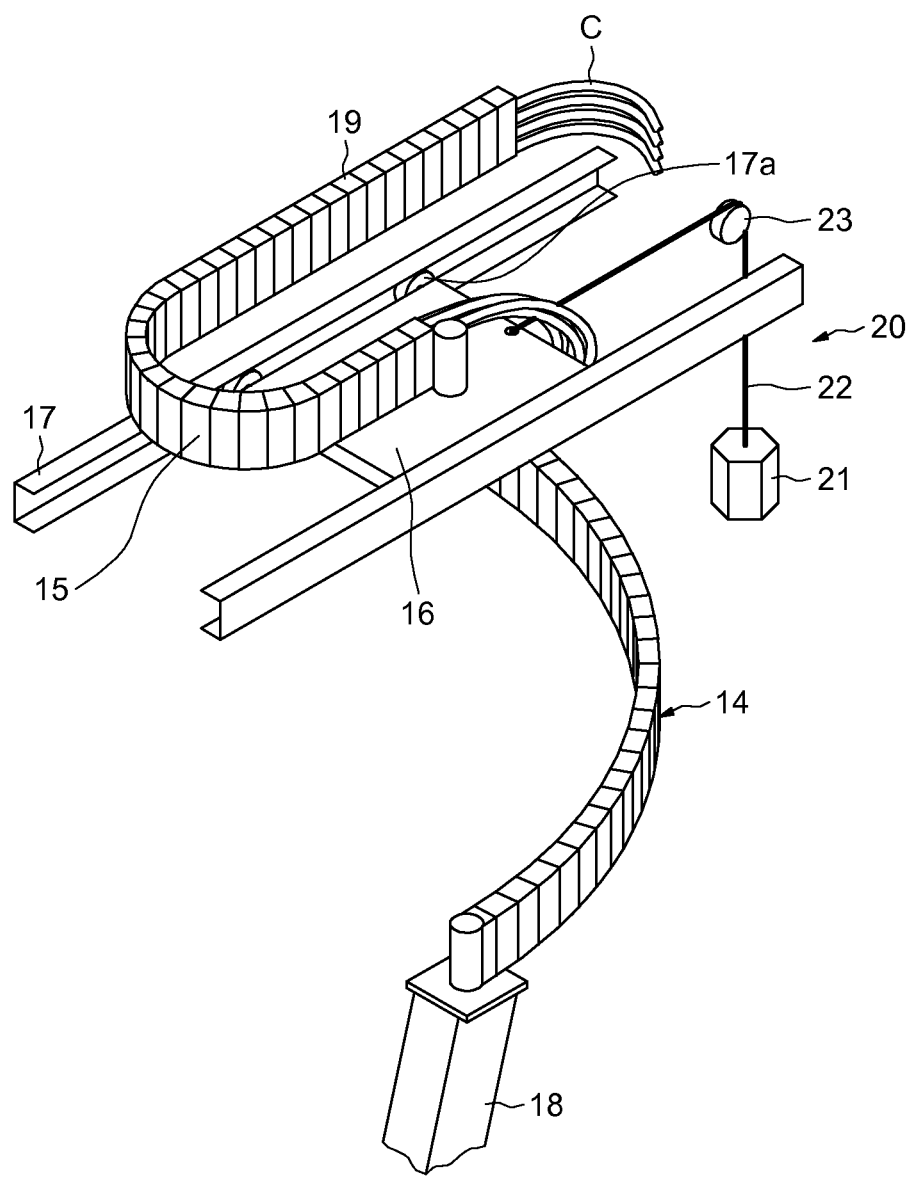
FIG. 2 shows in detail the device for supporting connection elements according to an embodiment of the present invention.

With reference also to FIG. 2, the chain 14 thus consists of a set of links 15 each articulated with other links about one or two vertical axes so that the articulation of the links and consequently the deformation of the chain occur in a single plane. The links are in particular articulated on one or two vertical or generally vertical axes so as to cause the chain to deform only in a substantially horizontal plane. Moreover, on either side of the articulation axis, the links 15 can be provided with lateral abutments making it possible to prevent excessive angular movements of the links which otherwise might cause blockages of the chain.

The supporting device also comprises a movable carriage 16 and a first set of guide rails 17, in this instance two in number, used to support and to guide the carriage 16. For example, the carriage 16 is provided with rollers, such as 17a, which run in the rails 17. For example, the rails 17 are attached to the ceiling of the operating room, substantially coaxially with the examination table 10 but, preferably, to the extent that they are intended only for supporting and for guiding the movable carriage, their end may be offset so that it is situated at a distance from the examination table 10 in order to prevent any opportunistic contamination of the patient.

It can also be seen in FIGS. 1 and 2 that the machine 1 is provided with an arm 18 erected for example from the support 7 to a height corresponding substantially to that of the carriage 16 minus the height of the chain 14. Thus, the chain 14 can be attached, by one of its ends, to the top end of the arm 18 and, by its other end, to the bottom face of the carriage 16, in the horizontal position.

The attachment means provided at the two ends of the chain may consist of pivot attachment means with vertical axis, so as to reduce the chain-deformation forces. Moreover, the device comprises a second chain 19, identical to the first chain 14, which receives the cables leaving the first chain 14, and of which one of the ends is fixed to the top face of the carriage 16, the opposite end being able to be fixed to a fixed support, for example a partition of the operating room, in order to run the connection cables to the equipment room.

A counterweight 20 may be provided comprising a weight 21 supported by a cable 22 and connected to the movable carriage 16 by means of a deflecting pulley 23, for example, attached to the wall of the room, so as to pull the carriage 16 into a storage position situated at one end of the rails 17, on the periphery of the room.

As can be understood, the return force exerted by the counterweight, in order to return the carriage 16 to the storage position, essentially only has to overcome the force of resistance to the deformation of the chain carrying the connection elements. It has been found that a light counterweight, for example of the order of about 4 kg (about 9 lbs), was sufficient to pull the movable carriage 16 into the storage position.

The embodiment that has just been described, which uses a chain with links articulated on a vertical axis, makes it possible to confine the connection elements of the X-ray machine in a horizontal plane situated in the vicinity of the ceiling of the operating room, and thus, prevents the connection elements from hanging down and thus hampering the movement of the various machines that the operating room contains or hampering the movement of the people that are working in the room.

Figure 3:
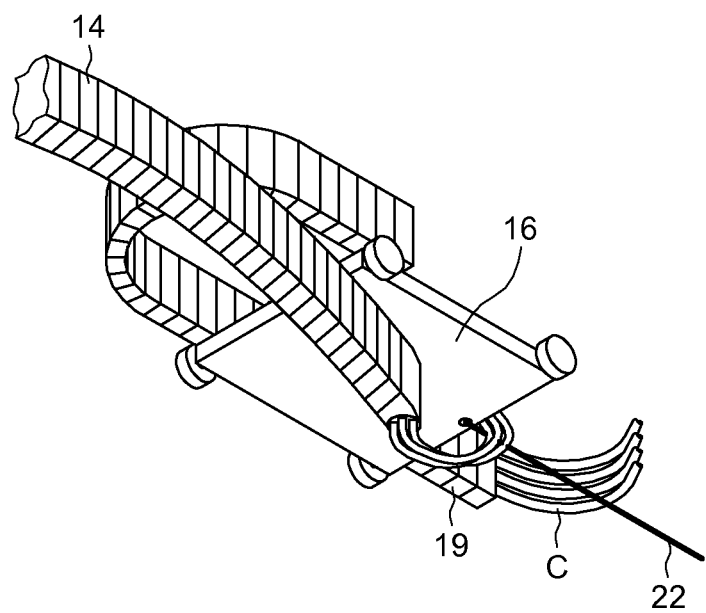
FIG. 3 is a detail view of the carriage of the device of FIG. 2 according to an embodiment of the present invention.

It will be noted however that the invention is not limited to the embodiment described. Specifically, in the embodiment described with reference to FIGS. 1, 2 and 3, the supporting device comprises a single set of rails 17 used to guide the carriage 16.

Figure 4:
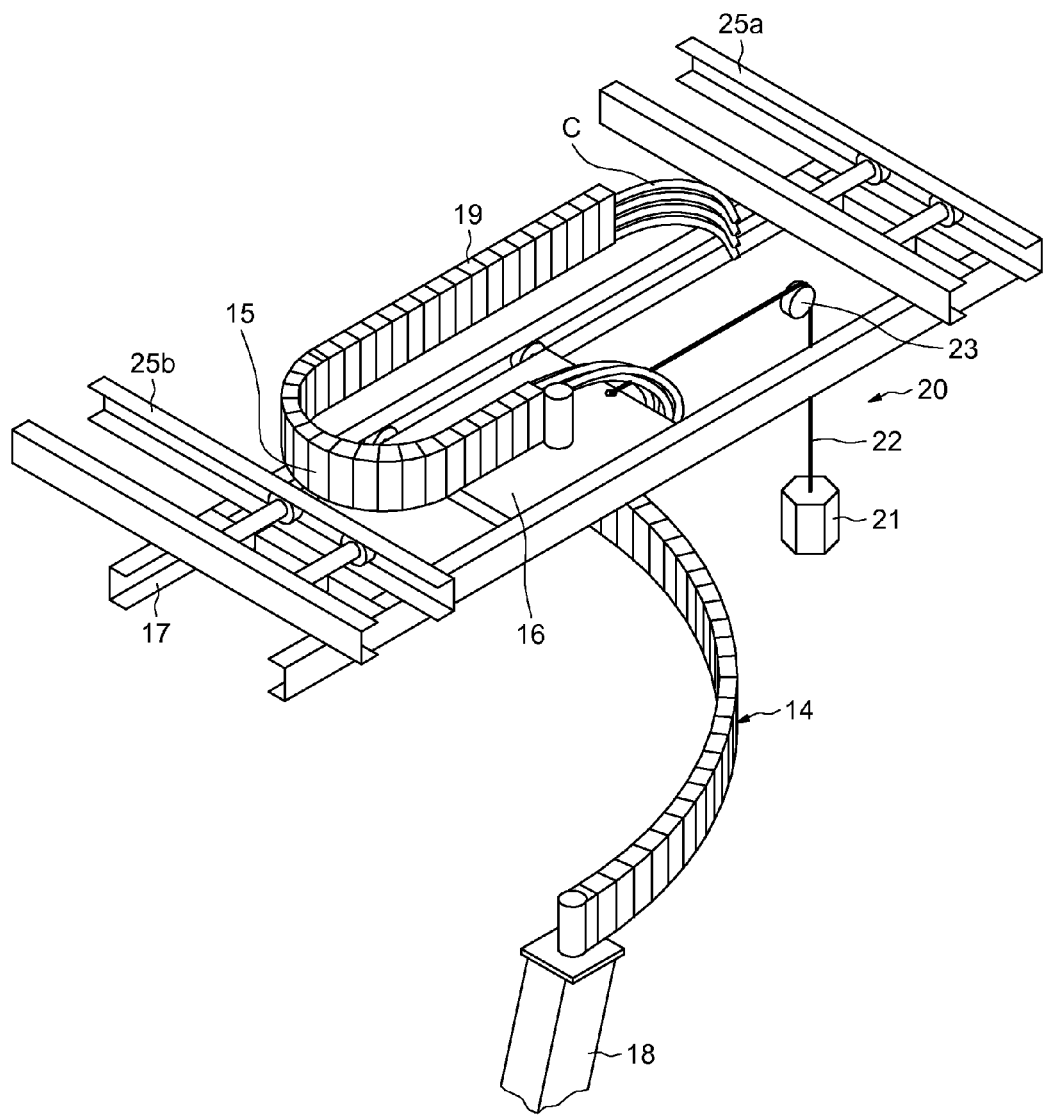
FIG. 4 shows an X-ray machine furnished with a device for supporting connection elements according to an embodiment of the present invention.

In another embodiment, that can be seen in FIG. 4, in which identical elements to those described above with reference to FIGS. 1 to 3 bear the same reference numbers, the cable-supporting device can be provided with a second set of rails, comprising in this instance two pairs of rails 25a and 25b extending in a different direction from the first set of rails, in this instance perpendicularly to the first set of rails.

In this embodiment, the rails of the first set of rails can be mounted on a support provided with rollers which run in the rails of the two pairs of rails 25a and 25b, or can be directly provided with such rollers in order to allow a transverse movement of the whole machine into a zone that is distant from the operating room.

Such an embodiment is advantageous for operating rooms that have several examination tables in order to be able to move the X-ray machine to face each of the tables. It will be noted finally that, in the envisaged embodiments, the X-ray machine is furnished with a mobile device provided with driving wheels. But naturally, there is no departure from the context of the invention when the machine is fitted with any other type of non-driving mobile device.

Embodiments of the present invention make it possible to confine the connection elements, notably the electric cables, the ducts for supplying the machine with cooling fluid and the data transmission channels, in the plane in which the chain can be deformed. In particular it is possible to position the chain high up and to confine the deformation of the chain in a horizontal plane.

What is claimed is:

1. A device for supporting connection elements of a mobile X-ray machine, the device comprising:
 a chain, an articulation and a deformation of which is confined to a single horizontal plane, the chain configured to contain the connection elements of the mobile X-ray machine in the single horizontal plane;
 a first set of at least one guide rail extending in a first guide direction; and
 a movable carriage mounted to the first set of at least one guide rail,
 wherein the chain comprises a first end configured to attach to an arm of the X-ray machine and an opposite end configured to attach to the movable carriage.

2. The device according to claim 1, comprising a second chain configured to contain connection elements, the second chain comprising a first end configured to attach to the movable carriage and an opposite end configured to attach to a fixed support,
 wherein an articulation and a deformation of the second chain is confined to the single horizontal plane.

3. The device according to claim 2, wherein at least one end of the second chain comprises a pivot attachment comprising a vertical pivot axis.

4. The device according to claim 1, wherein at least one end of the chain comprises a pivot attachment comprising a vertical pivot axis.

5. The device according to claim 1, further comprising a second set of at least one guide rail extending in a second guide direction different from the first guide direction, wherein the first set of at least one guide rail is mounted slidingly on the second set of at least one guide rail.

6. The device according to claim 5, wherein the first guide direction is perpendicular to the second guide direction.

7. The device according to claim 1, further comprising a counterweight capable of moving the movable carriage into a rest position at one end of the first set of at least one guide rail.

8. The device according to claim 1, wherein the articulation and the deformation of the chain is confined to the single horizontal plane and vertical movement of the chain and the connections elements contained by the chain is prevented.

9. The device according to claim 1, comprising a longitudinal cavity in the chain that is configured to contain the connection elements.

10. The device according to claim 1, wherein the chain comprises a plurality of articulated links confining the connection elements in the single plane.

11. The device according to claim 10, wherein each link in the plurality of articulated links is articulated with at least one other link about one or more vertical pivot axes, and wherein the articulation and the deformation of each link is confined to a horizontal axis in the single horizontal plane.

12. The device according to claim 11, comprising lateral abutments on either side of the horizontal axis of the chain, the lateral abutments configured to prevent angular movements of the plurality of links about the horizontal axis that exceed a predetermined angular movement.

13. An X-ray machine comprising:
 an X-ray tube;
 an X-ray detector placed opposite the X-ray tube in the direction of emission of the X rays;
 a movable device onto which the X-ray tube and the X-ray detector are mounted;
 an arm erected from the movable device; and
 a device for supporting connection elements of the X-ray machine, the device comprising a chain, an articulation and a deformation of the chain confined to a single horizontal plane, the chain configured to contain connection elements of the X-ray machine; and
 a connection device configured to attach the device at one end to the arm;
 wherein the device is configured to confine the connection elements within the single horizontal plane.

14. The machine according to claim 13, wherein the connection elements comprise:
 a set of electrical connection cables;
 at least one duct in which a cooling fluid for the machine circulates; and
 at least one data transmission channel.

15. The X-ray machine of claim 13, wherein movement of the chain in a vertical direction is prevented.

16. The X-ray machine of claim 13, wherein the chain comprises a plurality of articulated links, wherein each link in the plurality of articulated links is articulated with at least one other link about one or more vertical pivot axes, and an articulation of each link about the one or more vertical pivot axes is confined to the single horizontal plane.

17. The X-ray machine of claim 16, wherein one or more of a movement of the chain and the deformation of the chain in a vertical direction is prevented.

18. The X-ray machine of claim 16, wherein an articulation axis of the chain is the single horizontal plane, and wherein the device comprises lateral abutments on either side of the horizontal axis of the chain, the lateral abutments configured to prevent angular movements of the plurality of articulated links along the horizontal axis that exceed a predetermined angular movement.

* * * * *